(12) United States Patent
Kohanski et al.

(10) Patent No.: US 8,196,375 B2
(45) Date of Patent: Jun. 12, 2012

(54) HANDHELD TUBE CAPPER/DECAPPER

(75) Inventors: Jonathan Kohanski, Newburyport, MA (US); Daniel J. Seguin, Amherst, NH (US); Joseph DiCarlo, Chester, NH (US); Louis Franzini, Hudson, NH (US)

(73) Assignee: Matrix Technologies Corporation, Hudson, NH (US)

( * ) Notice: Subject to any disclaimer, the term of this patent is extended or adjusted under 35 U.S.C. 154(b) by 0 days.

(21) Appl. No.: 12/788,708

(22) Filed: May 27, 2010

(65) Prior Publication Data

US 2011/0289889 A1  Dec. 1, 2011

(51) Int. Cl.
*B67B 3/00* (2006.01)
*B65B 7/28* (2006.01)

(52) U.S. Cl. ............... 53/490; 53/471; 53/287; 53/317; 53/331

(58) Field of Classification Search .............. 53/471, 53/490, 287, 317, 318, 331, 331.5
See application file for complete search history.

(56) References Cited

U.S. PATENT DOCUMENTS

| | | | |
|---|---|---|---|
| 2,076,631 A | 4/1937 | Gantzer | |
| 3,031,822 A | 5/1962 | Dimond | |
| 4,030,271 A | 6/1977 | Kefauver et al. | |
| 5,061,449 A * | 10/1991 | Torti et al. | 422/525 |
| 5,115,617 A * | 5/1992 | Lewis et al. | 53/306 |
| 6,105,343 A | 8/2000 | Grove et al. | |
| 6,216,340 B1 | 4/2001 | Fassbind et al. | |
| 6,235,244 B1 | 5/2001 | Allen et al. | |
| 6,729,104 B2 * | 5/2004 | Marshall | 53/331 |
| 7,947,234 B2 * | 5/2011 | O'Connell et al. | 422/501 |
| 2003/0041560 A1 | 3/2003 | Kemnitz | |
| 2003/0223916 A1 * | 12/2003 | Testrut et al. | 422/104 |
| 2006/0130597 A1 | 6/2006 | Bernard et al. | |
| 2006/0236656 A1 * | 10/2006 | Bausch et al. | 53/167 |
| 2008/0016991 A1 * | 1/2008 | Gauthier | 81/474 |
| 2008/0022808 A1 | 1/2008 | Owen et al. | |

FOREIGN PATENT DOCUMENTS

| | | |
|---|---|---|
| DE | 296 12 501 U1 | 10/1996 |
| EP | 0 205 803 A1 | 12/1986 |
| EP | 1 882 949 A1 | 1/2008 |
| EP | 2 031 407 A1 | 3/2009 |
| GB | 2 010 789 A | 7/1979 |
| GB | 2 129 409 A | 5/1984 |
| GB | 2359069 A * | 8/2001 |
| JP | 02152632 A * | 6/1990 |
| WO | 2005/110600 A2 | 11/2005 |
| WO | 2006/029083 A2 | 3/2006 |

OTHER PUBLICATIONS

European Patent Office, European Search Report and Written Opinion, Application No. 11167260.6-1261, mailed Sep. 26, 2011.

* cited by examiner

*Primary Examiner* — Hemant M Desai

(74) *Attorney, Agent, or Firm* — Wood, Herron & Evans, LLP

(57) ABSTRACT

A tube capper and decapper and method of using the same. The tube capper includes a handheld housing that supports a one-dimensional array of spindles. Each spindle is shaped to receive a cap. A drive mechanism rotates each spindle of the one-dimensional array in unison for capping or decapping a corresponding one-dimensional array of tubes.

13 Claims, 14 Drawing Sheets

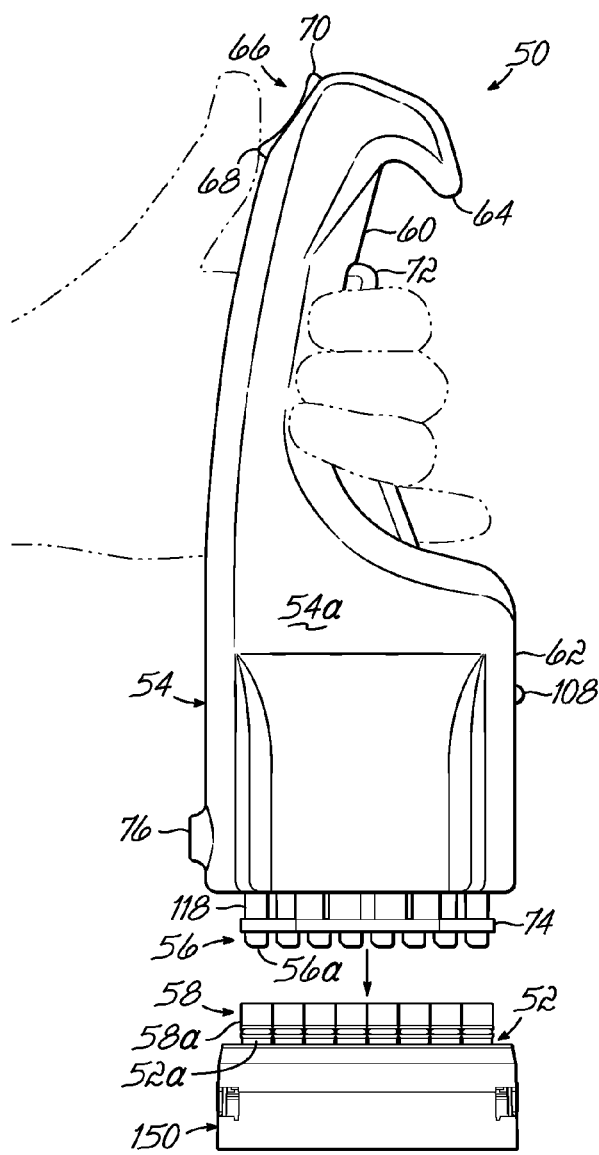
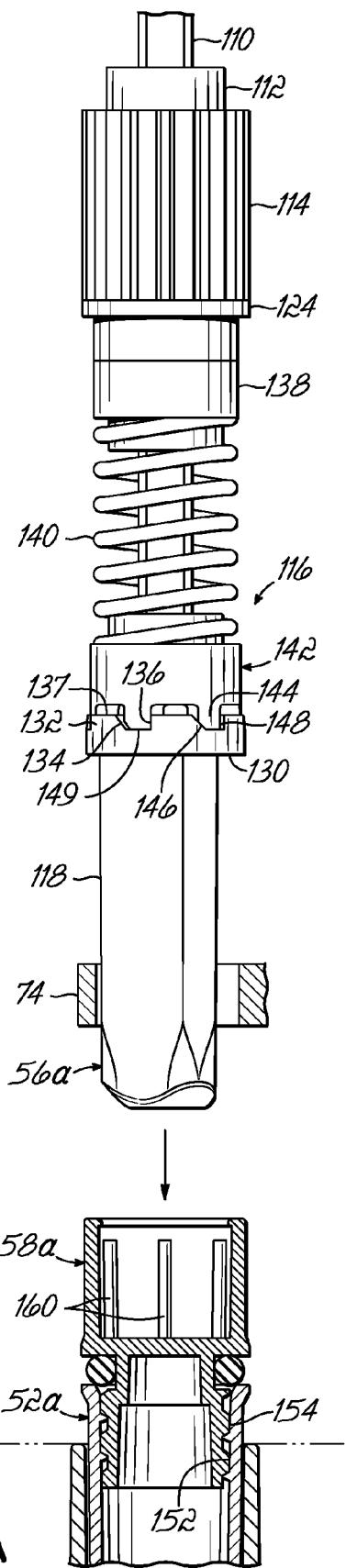
FIG. 7
FIG. 7A

HANDHELD TUBE CAPPER/DECAPPER

FIELD OF THE INVENTION

The present invention relates generally to devices and methods for capping and decapping tubes and, more specifically, to a device and method for capping and decapping an array of receptacles, such as microtubes.

BACKGROUND OF THE INVENTION

Chemical investigations are often carried out on a microvolume scale within microtubes that are configured to hold, by way of example, 0.25 mL to 2 mL of volume. These tubes allow the investigator to test several combinations or reactions at a single time without large volumes or expense. The tubes may be capped and stored as arrays in racks of 16 to 96 tubes each. Conventionally, capping and decapping of tubes was accomplished individually by hand when the addition of reagents or withdrawal of the sample was necessary. Recently, multi-channel pipetters have allowed technicians to work simultaneously with multiple tubes at a time. Still, capping and decapping was accomplished manually.

More recently, table top capper and decapper devices have been designed that cap and decap the full two-dimensional array of tubes within a rack. However, these devices are large, bulky, costly, and operable only with respect to all caps from all tubes within the rack. Often, it is necessary to add reagents to only a subset of the tubes within the rack and/or to limit the samples exposure to air.

Accordingly, it would be of great benefit to provide a smaller, more cost effective manner of capping/decapping a subset of tubes within the rack.

SUMMARY OF THE INVENTION

The present invention overcomes the foregoing and other shortcomings and drawbacks of a tube capper and decapper heretofore known for use in capping and decapping an array of tubes or other receptacles. While the invention will be described in connection with certain embodiments, it will be understood that the invention is not limited to these embodiments. On the contrary, the invention includes all alternatives, modifications and equivalents as may be included within the spirit and scope of the present invention.

The present invention is directed to a capper and decapper device having a handheld housing that supports a one-dimensional array of spindles. Each spindle of the array cooperates with a cap used to close an open end of a tube. A drive mechanism of the device simultaneously rotates each spindle of the one-dimensional array in two opposite directions, e.g., forward and reverse. One direction of rotation of the spindles is used to tighten a plurality of caps onto a plurality of tubes or receptacles. The other, opposite direction of rotation of the spindles is used to loosen and decap the plurality of caps from the plurality of tubes.

A method of capping a tube using the handheld device is also described. According to one embodiment, the method includes the step of manually directing the handheld device to and into a plurality of caps, thereby coupling the plurality of caps to the one-dimensional array of spindles. The handheld device, with the plurality of caps retained on the one-dimensional array of spindles, is manually transferred to a one-dimensional array of tubes. By simultaneously rotating the one-dimensional array of spindles in one direction, the plurality of caps is applied to the one-dimensional array of tubes. The handheld device may then be separated from the one-dimensional array of capped tubes.

According to another aspect of the present invention, a method of decapping a tube using the handheld device is described. The method includes the step of manually directing the handheld device to a one-dimensional array of capped tubes. Each spindle of the one-dimensional array of spindles is coupled to the plurality of caps. By simultaneously rotating the one-dimensional array of spindles in an opposite direction, the caps are removed from the one-dimensional array of tubes. The handheld device, with the plurality of caps retained by the one-dimensional array of spindles, is manually transferred away from the one-dimensional array of tubes. The plurality of caps is then separated from the one-dimensional array of spindles.

According to yet another aspect of the present invention, a capper/decapper device that includes at least one spindle is described. The at least one spindle includes a spigot that has a notched ring coupled thereto. The notched ring has a plurality of notches, and each notch includes a sloped side and a generally vertical side. The at least one spindle also includes a clutch mechanism, which includes a compression device and a slip gear. The slip gear is operably coupled to the compression device and cooperates with the notched ring. The slip gear includes a plurality of teeth, each tooth having a sloped side and a generally vertical side. During a capping operation, the notched ring and the slip gear rotate together in fixed relationship relative to each other. When the torsional force applied by the slip gear to the notched ring exceeds a predetermined torque, the slip gear rotates relative to the notched gear.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIGS. 7 and 8 are side elevational views illustrating successive steps of the handheld device engaging and decapping the one-dimensional array of tubes.

FIGS. 7A and 8A are enlarged side elevational views illustrating successive steps of one spindle engaging and decapping a tube, shown in cross-section.

DETAILED DESCRIPTION OF THE INVENTION

Figure 1:
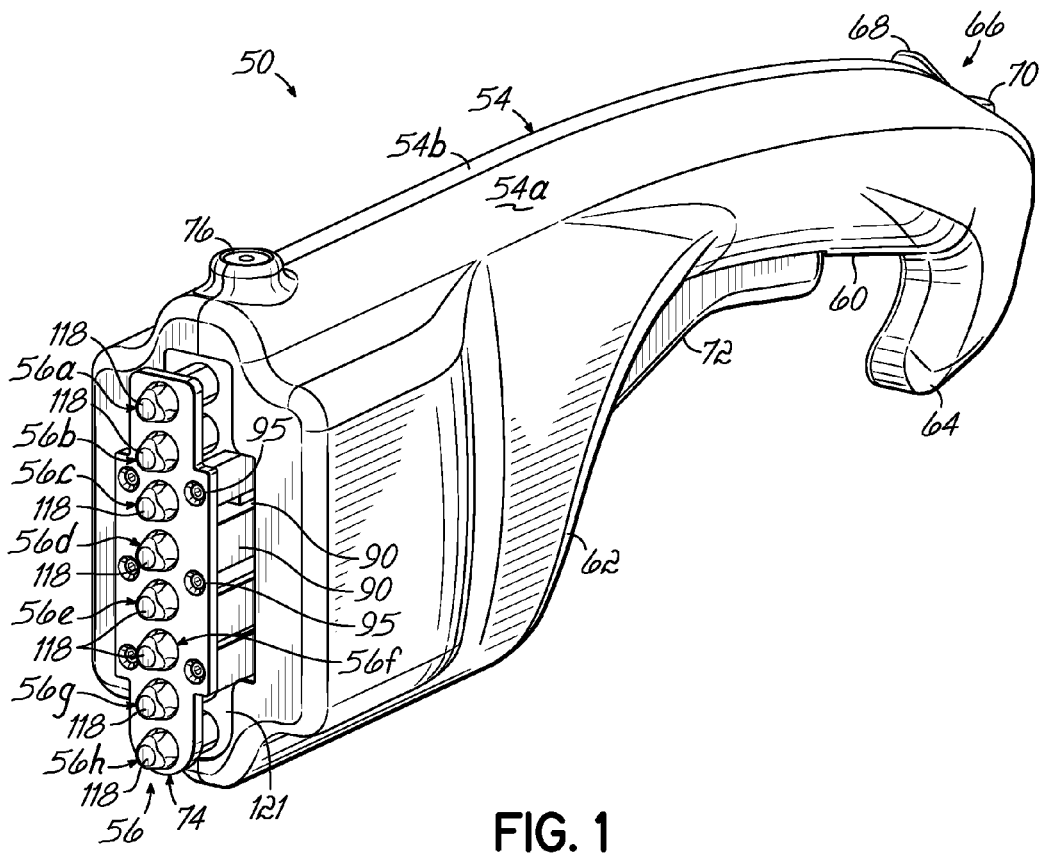
FIG. 1 is a perspective view of one exemplary embodiment of a handheld device for capping and decapping a one-dimensional array of tubes.

Referring now to the figures, and to FIG. 1 in particular, a handheld device 50 according to one embodiment of the present invention is shown for capping and decapping a one-dimensional array of receptacles that may be used to hold and/or store a sample. Receptacles may vary in size and shape according to the particular application and may include a one-dimensional array of tubes 52 such as those shown in FIG. 6, by way of example and without limitation thereto. The device 50 includes a handheld housing 54 that supports a one-dimensional array of spindles 56 that are configured to cooperate with caps $58_a$-$58_h$ (FIG. 6) as will be described in detail below.

The housing 54 may include an ergonomic design that facilitates grasping and operation of the device 50 by a wide range of user hand sizes as shown in FIG. 7. In this way, the handheld device 50 may be manually manipulated by a user in a plurality of different orientations during capping and decapping operations.

In one embodiment, the device 50 has a neck 60 that extends from a base portion 62 housing the one-dimensional array of spindles 56. The neck 60 may be shaped to be grasped by a user wrapping the user's hand around the neck 60, with the one-dimensional array of spindles 56 extending downwardly during a capping or decapping operation. The housing 54 may be molded as two housing parts 54a, 54b from a polymeric material that are then joined together by fasteners, such as screws, bolts, rivets, or any other suitable means.

The neck 60 may include a hook portion 64 for hanging and/or storage of the device 50 when it is not in use, and also to aid in the ergonomic handling of the device 50. The neck 60 may further include two triggers. A first trigger 66 may be located on the neck 60 near the hook portion 64 in a manner to be thumb operated by a user via a two-way rocker switch having first and second actuating positions 68, 70. In the first actuating position 68, the two-way rocker switch may operate the device 50 in a capping mode while in the second actuating position 70 the two-way rocker switch may operate the device 50 in a decapping mode. The two-way toggle switch may be constructed from a polymeric material in the form of a single button design for ease of use by the user's thumb. Of course, other switch designs are possible as well, such as two separate buttons or switches, or any other suitable actuating mechanism.

A second trigger 72 may be positioned on the neck 60 in a manner to be palm-operated by the user as a squeeze trigger. Once squeezed, the second trigger 72 operates an ejection plate 74, described in greater detail below, for removing or separating the caps 58 (FIG. 6) from the one-dimensional array of spindles 56.

As also shown in FIG. 1, the device 50 may further include a charging connector 76 that is configured to receive a connector of a charger (not shown) for supplying power to an internally located power source 78 (FIG. 2A), such as one or more batteries. Suitable power source(s) 78 (FIG. 2A) may include rechargeable batteries or replaceable alkaline batteries. Alternatively, the device 50 may be powered by an external power source (not shown), including an electrical plug connected to an electrical outlet (not shown). When a rechargeable power or external electrical power supply is used, the charging connector 76 may receive a jack coupled to an AC adaptor (not shown).

Figure 2A:
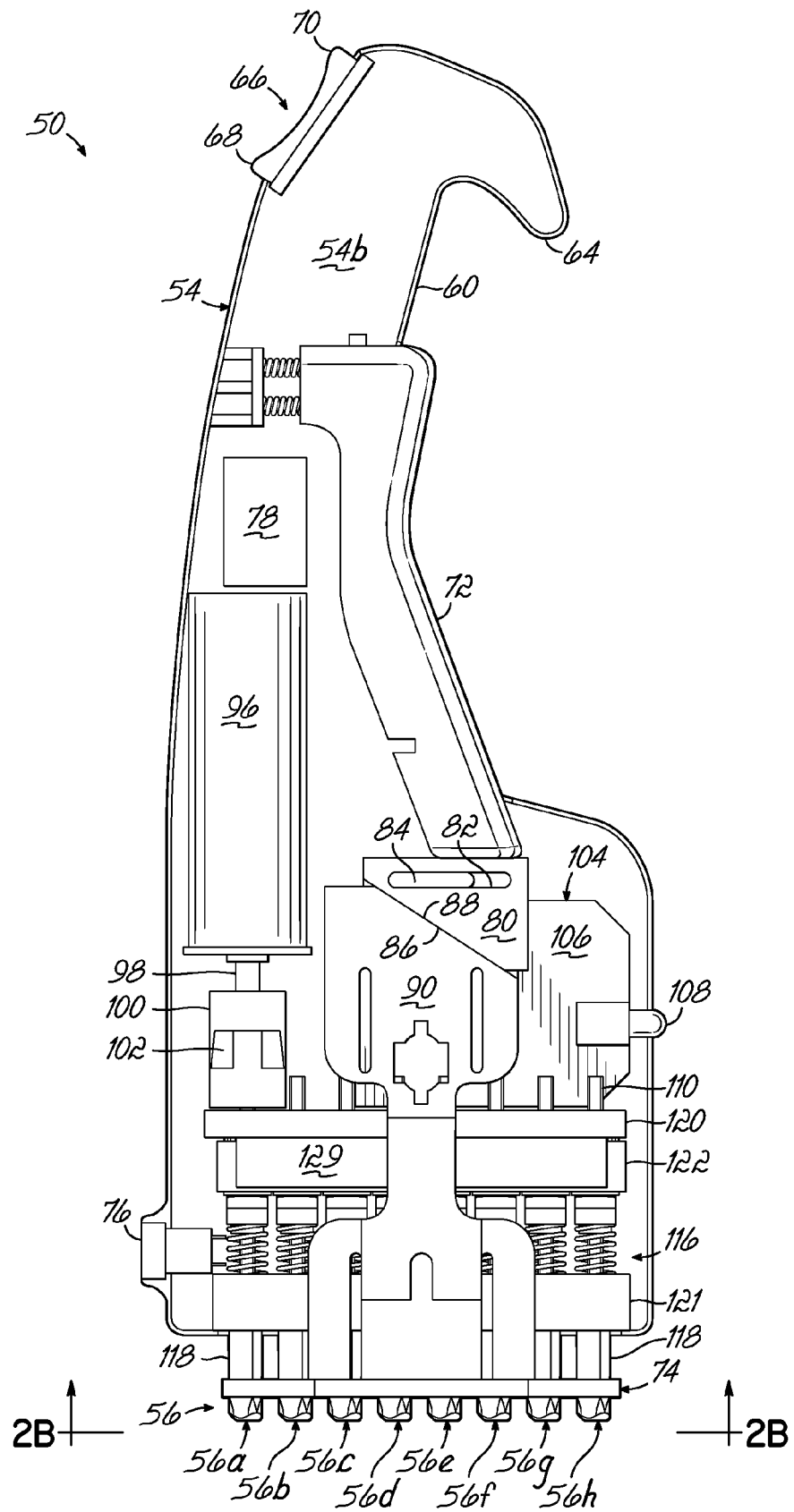
FIG. 2A is a general cross-sectional view of the handheld device of FIG. 1.

Turning now to FIG. 2A, wherein one housing part 54a is removed to illustrate various internal components of the device 50 according to one embodiment. As shown, one end of the second trigger 72 may be affixed to a slider plate 80 that includes a slit 82. The slit 82 receives, and is in sliding relation to, a projection 84 provided on the second housing part 54b. The slider plate 80 includes an angular edge 86 that cooperates with an angular edge 88 provided on an extension plate 90 that is operatively coupled to the ejection plate 74. The cooperating angular edges 86, 88 operate to convert the generally horizontal sliding motion created by manual squeezing of the second trigger 72 to a generally vertical translation motion of the ejection plate 74 when the device 50 is held in the orientation shown in FIG. 2A. More specifically, as the second trigger 72 is squeezed, the slider plate 80 moves laterally, from right to left in FIG. 2A, so as to translate the extension plate 90 downwardly in a direction that is normal to the direction of the lateral movement of the slider plate 80. As a result of this downward movement of the extension plate 90, the ejection plate 74 also moves downwardly so as to apply a force to a top portion of the caps 58 to eject the caps 58 from the spindle 56 as described in detail below.

Figure 2B:
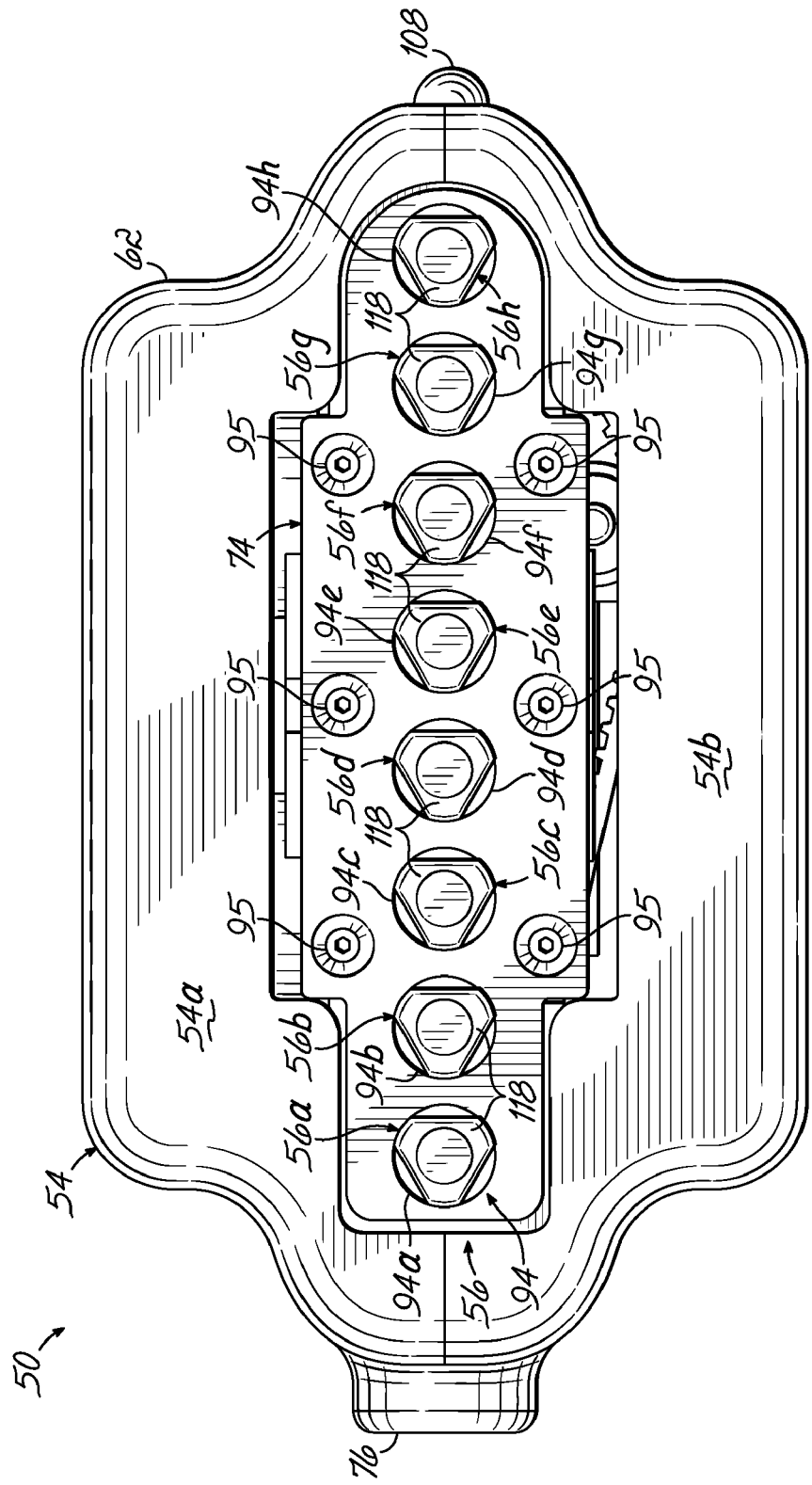
FIG. 2B is a bottom view of an ejection plate, taken along the line 2B-2B of FIG. 2A.

The ejection plate 74, shown in greater detail in FIG. 2B, includes an array of openings 94 that are aligned respectively with the one-dimensional array of spindles 56. Accordingly, each opening $94_a$-$94_h$ of the array 94 has a diameter that is greater than the outer diameter of each spindle $56_a$-$56_h$ such that the spindles $56_a$-$56_h$ extend through the respective openings $94_a$-$94_h$. However, the diameter of each opening $94_a$-$94_h$ is sized to be less than an outer diameter of the caps 58. The ejection plate 74 may be constructed from a polymeric or metallic material and may be glued, epoxy, riveted, screwed (screws 95 shown), or otherwise affixed to the extension plate 90.

Figure 2C:
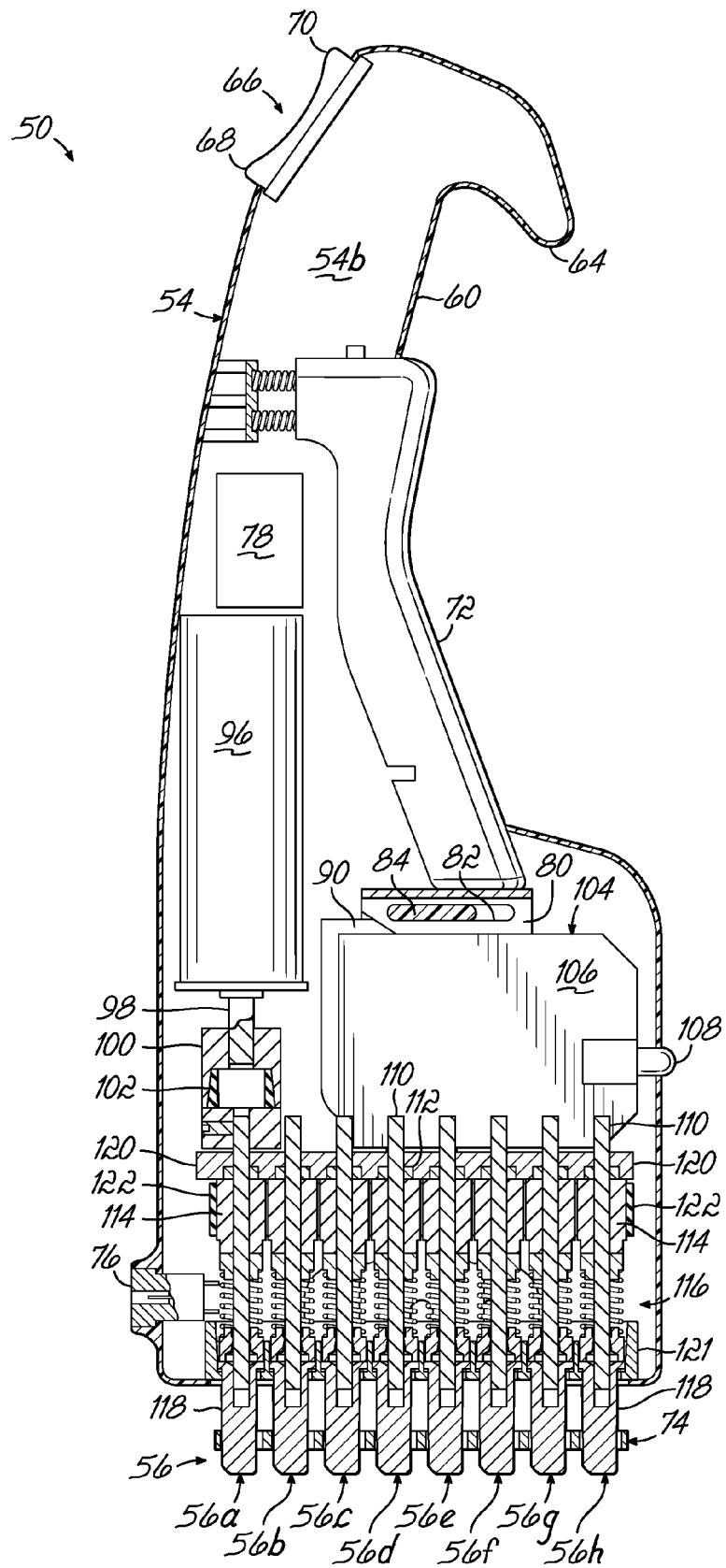
FIG. 2C is a side elevational view of the internal components of the handheld device with the ejection plate removed, shown in cross-section.

Referring now to FIG. 2C, where the ejection and extension plates 74 and 90 have been removed for clarity, a rotary motor 96 having a drive shaft 98 is supported within the housing 54 according to one embodiment. The drive shaft 98 is operatively coupled to a first spindle $56_a$ of the one-dimensional array 56 by way of a motor coupling 100. Suitable motor couplings, such as the one illustrated, may include an elastomer insert 102 that dampens vibrations, is electrically insulated, and backlash free; however, other motor couplings may be used. The motor 96 may be electrically operated by the first trigger 66, which is configured to operate the motor 96 in both forward (capping) and reverse (decapping) directions.

One or both of the motor 96 and first trigger 66 may be coupled to a controller 104. The controller 104 may be configured to operate and/or manage the operation and charging of the handheld device 50. In the illustrative embodiment, the controller 104 is shown to include a circuit board 106 for electrically coupling the motor 96 to the power source 78. In some embodiments, the controller 104 may be programmable, for example, in one programmable mode the device 50 may be configured to enter a sleep mode after a period of nonuse to reserve the power supply charge.

An indicator, illustrated as an LED 108 according to one embodiment, may also be coupled to the circuit board 106 and may be operable to indicate a charging or operational status of the device 50.

Figure 3:
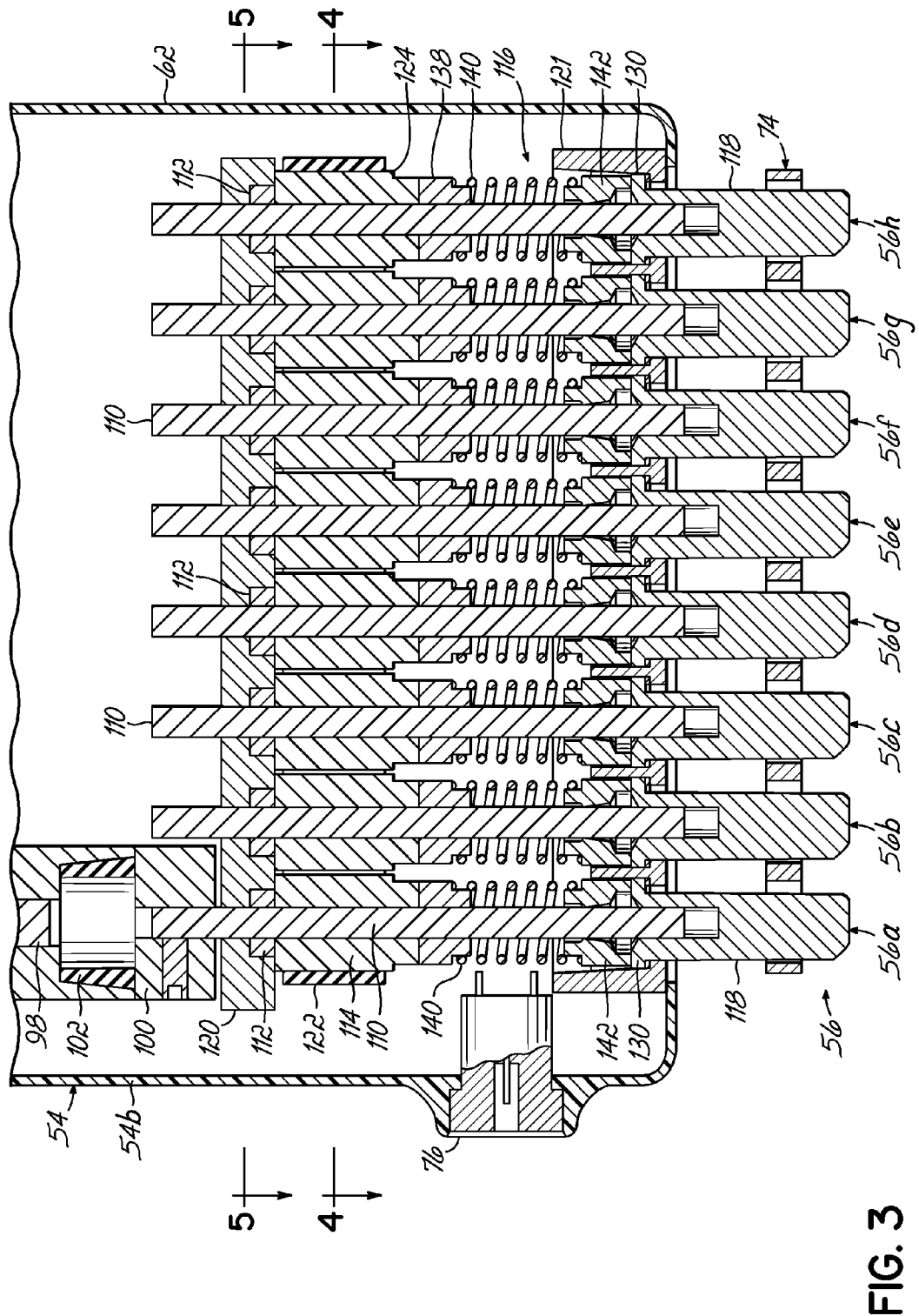
FIG. 3 is an enlarged cross-sectional view of a one-dimensional array of spindles of the handheld device of FIG. 1.

FIG. 3 illustrates the one-dimensional array of spindles 56 in greater detail. Each spindle $56_a$-$56_h$ includes a shank 110 that may be keyed, for example, with a cross-section shaped as a circle truncated by two cords. Further, it would be readily understood that two-dimensional arrays could also be used if desired. Each shank 110, as shown, also includes a cap 112, a gear portion 114, a clutch mechanism 116, and a spigot 118. It would be understood that operation of the one-dimensional array of spindles 56 is not limited to each spindle $56_a$-$56_h$ including a cap 112. Instead, it is possible that one or more spindles $56_a$-$56_h$ of the one dimensional array may actually include a cap 112, such as in the occasion when only a portion of the one-dimensional array of tubes 52 (FIG. 6) holds a sample requiring capping and/or decapping. A shank support 120 with a bucket support 121 support each shank 110 in an upright position and aligns each shank 110 in the one-dimensional array of spindles 56 within the housing 54.

While FIG. 3 illustrates the one-dimensional array of spindles 56 consisting of eight separate spindles $56_a$-$56_h$, it would be understood that any number of spindles may be used and may indeed range from a single spindle to arrays consisting of more than eight spindles, for instance twelve spindles. Further, FIG. 3 illustrates adjacent ones of the spindles $56_a$-$56_h$ being separated by a fixed uniform spacing along the length of the array 56. In one embodiment, the fixed, uniform spacing between adjacent ones of the spindles $56_a$-$56_h$ may range between about 9 mm and about 12 mm, although other spacings are possible as well. However, the one-dimensional array 56 should not be construed to be so limited. Instead, other embodiments are envisioned that would allow adjacent ones of the spindles $56_a$-$56_h$ to be separated by a non-uniform spacing between adjacent ones of the spindles 56a-56h and along the length of the array 56.

Figure 6:
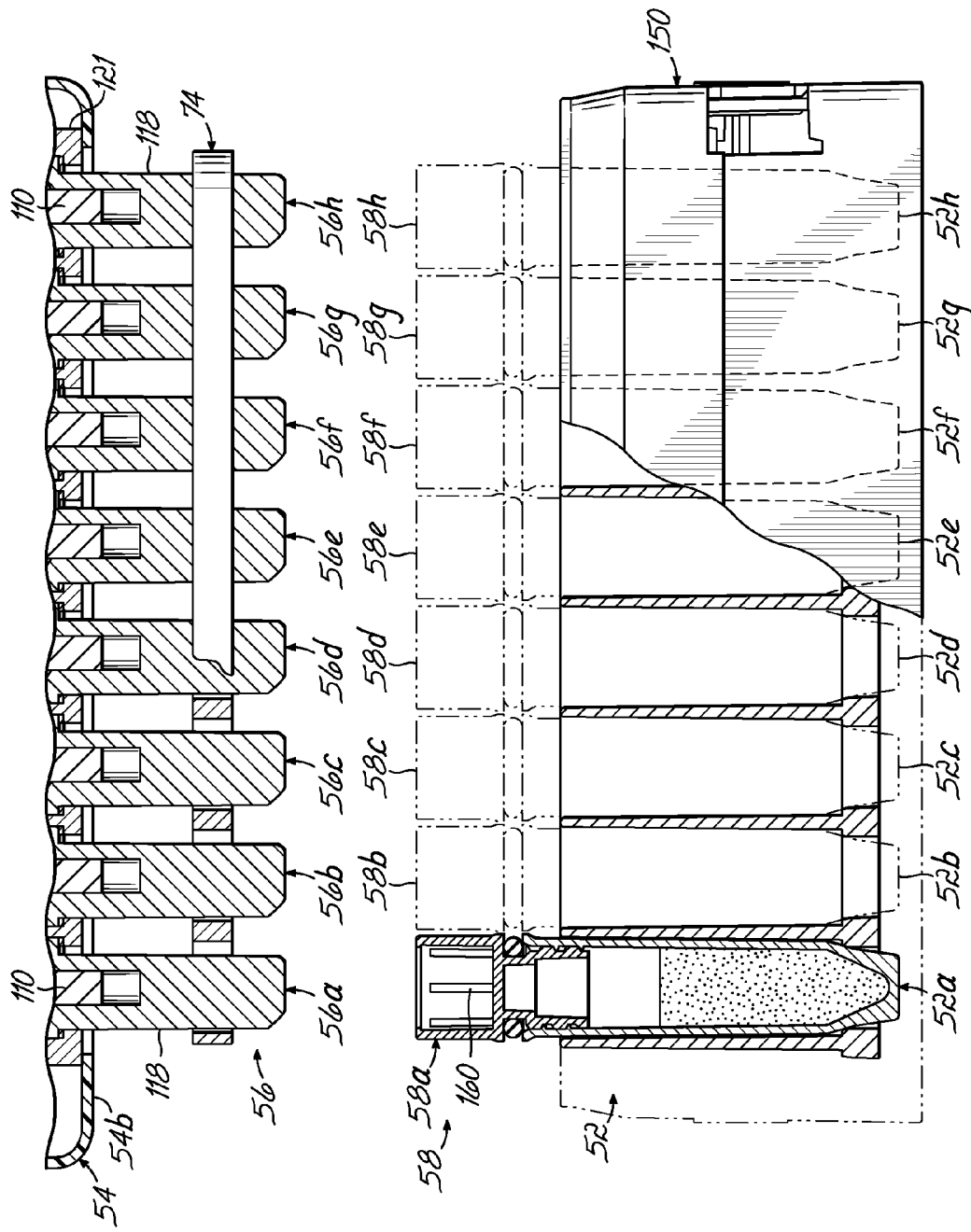
FIG. 6 is an enlarged side elevational view, in partial cross-section, of the one-dimensional array of spindles positioned to engage a one-dimensional array of capped tubes.

According to another aspect, the invention may include structure that enables the investigator to vary the spacing between adjacent ones of the spindles $56_a$-$56_h$ of the one-dimensional array 56. For example, suitable structures for uniformly but variably adjusting the spacings between adjacent ones of the spindles $56_a$-$56_h$ may include those described in U.S. Pat. No. 6,235,244, issued to Allen et al. on May 22, 2001, and entitled "Uniformly Expandable Multi-Channel Pipettor," the disclosure of which is incorporated herein by reference in its entirety. One of ordinary skill in the art would readily appreciate that other structures may be used to adjust uniformly, or even non-uniformly, variable spacings between the adjacent ones of the spindles $56_a$-$56_h$. According to this embodiment, the spacing between adjacent ones of the spindles $56_a$-$56_h$ may be uniform, but variable, with spacings ranging from about 4.5 mm and 14 mm, by way of example. Enabling the variable spacing between adjacent ones of the spindles $56_a$-$56_h$ allows the investigator to adapt the use of the handheld device 50 according to different tray designs used in holding and/or storing the tubes $52_a$-$52_h$ (FIG. 6).

Figure 4:
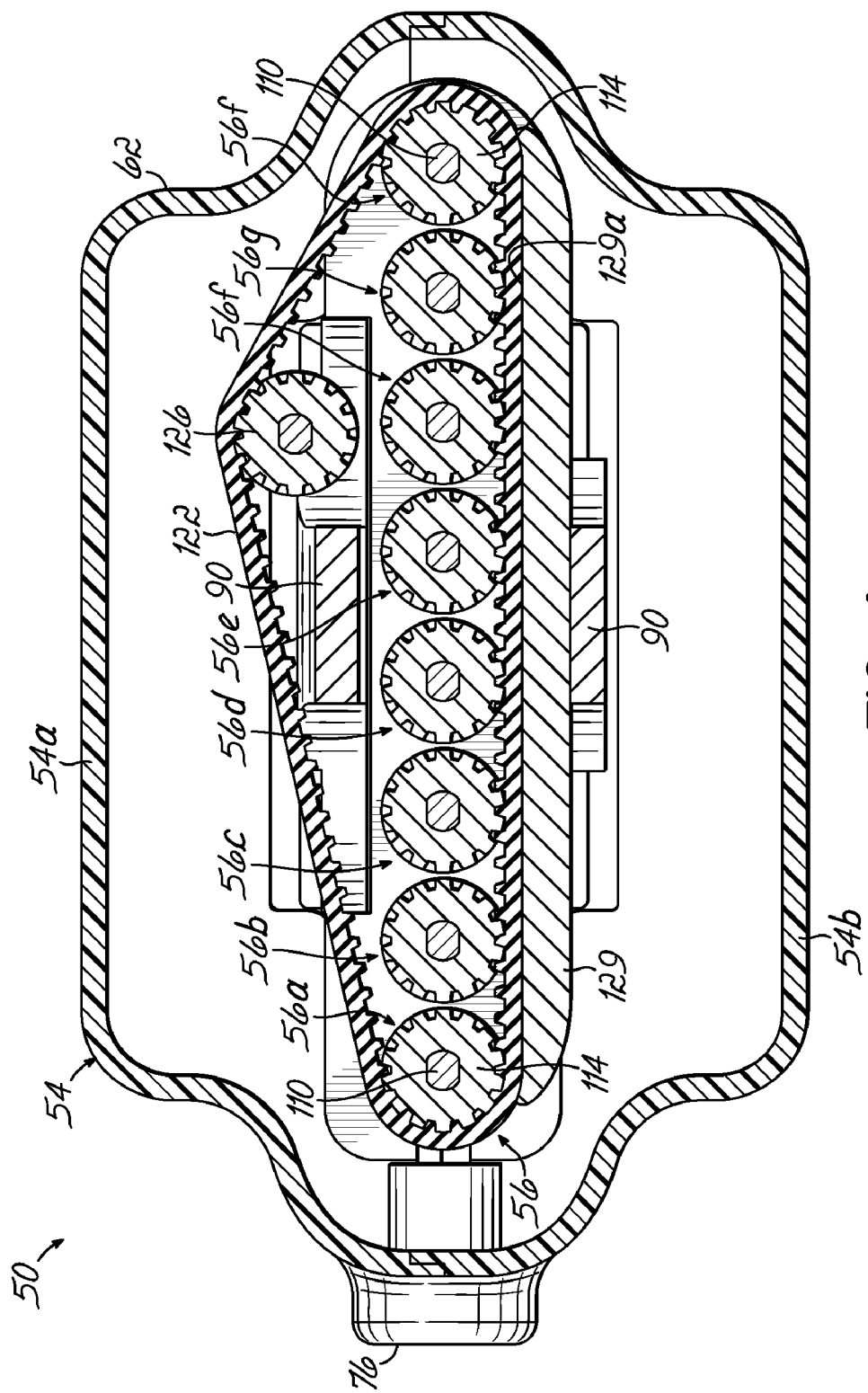
FIG. 4 is a cross-sectional view of one exemplary embodiment of a drive mechanism for operating the array of spindles, taken along the line 4-4 of FIG. 3.

With continued reference to FIGS. 3 and 4, the details of the gear portions 114 are shown in greater detail. Generally, an inner diameter of each gear portion 114 may be keyed to match the shape of the shank 110 so as to rotate with rotation of the shank 110. The gear portions 114 engage a toothed belt 122 that is operable to translate the rotation of the drive shaft 98 (FIG. 2C) and first spindle $56_a$ to the other spindles $56_b$-$56_h$ comprising the array 56. In this way, all spindles $56_a$-$56_h$ in the one-dimensional array 56 may rotate in unison. The toothed belt 122 may ride along a shelf 124 on each of the gear portions 114, which aids in preventing the toothed belt 122 from disengaging from the gear portions 114.

Figure 5:
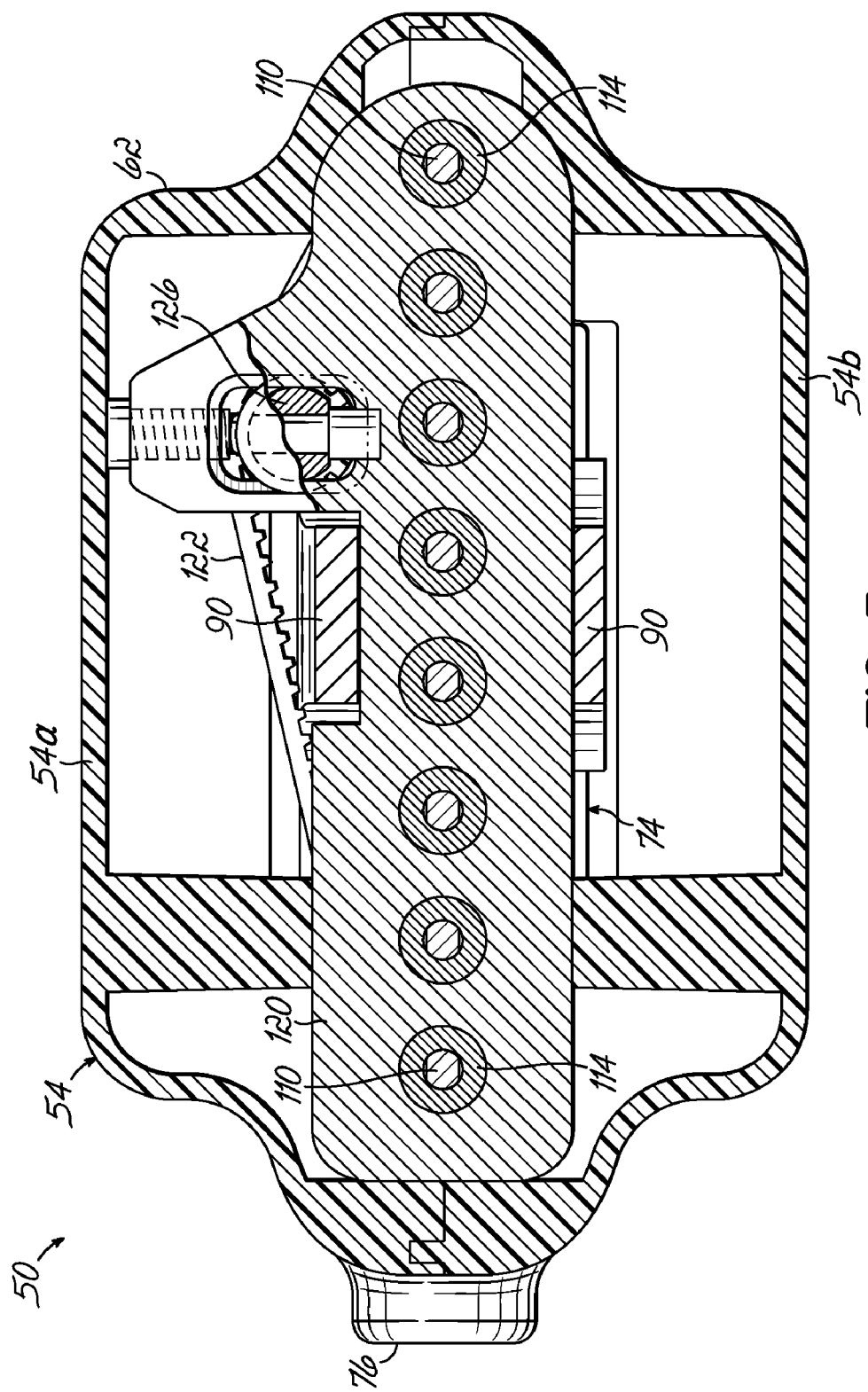
FIG. 5 is a cross-sectional view of one exemplary embodiment of a tensioning device for the drive mechanism, taken along the line 5-5 of FIG. 3.

FIG. 4 further illustrates a tensioning gear 126 that is offset from the one-dimensional array of spindles 56 and that also engages the toothed belt 122. The tensioning gear 126 is operable in maintaining a level of tension on the toothed belt 122 such that the rotational force of the drive shaft 98 (FIG. 2C) and first spindle $56_a$ are efficiently transferred to all spindles $56_b$-$56_h$ of the array 56. Tensioning of the tensioning gear 126 may be adjusted by a tension mechanism 128 known to those of ordinary skill in the art and as shown in FIG. 5.

Also shown in FIG. 4 is a device, illustrated as a belt backer 129, for firmly retaining the toothed belt 122 against the gear portions 114 of the spindles $56_a$-$56_h$. A contact surface 129a of the belt backer 129 is configured to contact and retain the toothed belt 122 firmly against all gear portions 114 of the spindles 56a-56h, to further prevent the toothed belt 122 form disengaging from the gear portions 114, and to ensure that all spindles $56_a$-$56_h$ rotate uniformly without slipping. One of ordinary skill in the art would readily appreciate that other devices, including low-friction mechanisms, may be used to retain the belt 122, including roller pins or bearings as non-limiting examples.

Turning now to FIG. 6, the spigots 118 are shown in a position ready for engaging the one-dimensional array of tubes 52. The tubes $52_a$-$52_h$ may be, for example, the Matrix 2D Barcoded ScrewTop Storage Tubes commercially available for Thermo Fisher Scientific of Hudson, N.H., which are generally constructed of a polypropylene material and constructed for holding 500 μL or 1.0 mL sample sizes. The tubes $52_a$-$52_h$ may be purchased in bulk or within a tray 150 containing of 96 tubes situated in an array of 8×12. Each tube $52_a$-$52_h$ includes a screw thread 152 for receiving a cap $58_a$-$58_h$ that may be constructed from a polypropylene material and molded to include matching thread pattern 154. The caps $58_a$-$58_h$ may be molded to include external gripping ridges (not shown) for facilitating manual removal of the cap 58 from the tube 52 and internal ribs 160, or other suitable keying structure, for capping and decapping by a capper/decapper such as device 50.

Referring again to FIG. 3, and with particular reference to FIG. 7A, the details of the spindle $56_a$ are shown. The spigots 118 are positioned on the terminal ends of the spindles $56_a$-$56_h$. In the orientation shown in FIG. 7A, an upper portion of each spigot 118 includes an annular notched ring 130 coupled thereto either by being integral with the spigot 118 or attached to the spigot 118 through suitable means. Each notch 132 of the notched ring 130 has a downwardly sloped side 134 and a generally vertical side 136. The generally vertical side 136 is formed to be substantially at a 90° angle with respect to a generally horizontal upper surface 137 of the notched ring 130 while the angle of the downwardly sloped side 134, indicated as angle "α" in FIG. 8B, may range from between about 30° and about 60°, and preferably about 45°, with respect to generally horizontal upper surface 137 of the notched ring 130. Selection of angle "a" is dependent on several factors, including various inherent material characteristics of the clutch mechanism 116, as described below, and a desired amount of torque to be applied to the caps 58.

Each notched ring 130 cooperates with the clutch mechanism 116 of the respective spindle $56_a$-$56_h$. The clutch mechanism 116 generally includes an upper portion 138 located below the gear portion 114, a compression device (shown herein as a compression spring 140), and a slip gear 142 that engages the notched ring 130 of the spigot 118. The spring 140 is located about the shank 110 between the upper portion 138 and the slip gear 142. Both the upper portion 138 and the slip gear 142 include an inner diameter that is keyed to the shank 110 so as to rotate with rotation of the spindles $56_a$-$56_h$. Construction of the spring 140 may be selected from various materials, such as metallic or polymeric materials, so as to include a desired spring constant. Various physical aspects of the compression spring 140 may be selected to provide a desired spring constant, including the material of the spring, the number of coils, the pitch of the coils, the diameter of the coils, and other spring characteristics appreciated by those of ordinary skill in the art. In one embodiment, spring constants generally ranging from about 10 lbs/in to about 15 lbs/in, and preferably about 13.8 lbs/in, may be employed to provide a suitable level of torque to the caps 58.

The slip gear 142 floats vertically on the shank 110 and is biased downwardly by the spring 140 toward the notched ring 130 of the spigot 118. The slip gear 142 includes a number of teeth 144 that correspond to, and are shaped in cooperating relationship with, the notches 132 of the notched ring 130. In that regard, each tooth 144 includes a downwardly sloped side 146 and a generally vertical side 148. The generally vertical side 148 is formed to be at a substantially 90° angle with respect to a generally horizontal lower surface 149 of the slip gear 142, while the angle of the downwardly sloped side 146, indicated by angle "β" in FIG. 11B, may range between about 30° and about 60°, and preferably about 45°, with respect to the generally horizontal lower surface 149 of the slip gear 142. The teeth 144 of the slip gear 142 are received in the notches 132 of the notched ring 130 of the spigot 118.

Referring now to FIGS. 7, 7A, 8, and 8A, the exemplary manner of using the handheld device 50 to decap the array of tubes 52 is shown. In FIGS. 7 and 7A, the handheld device 50 is positioned ready for engaging the array of capped tubes 52.

Figure 8C:
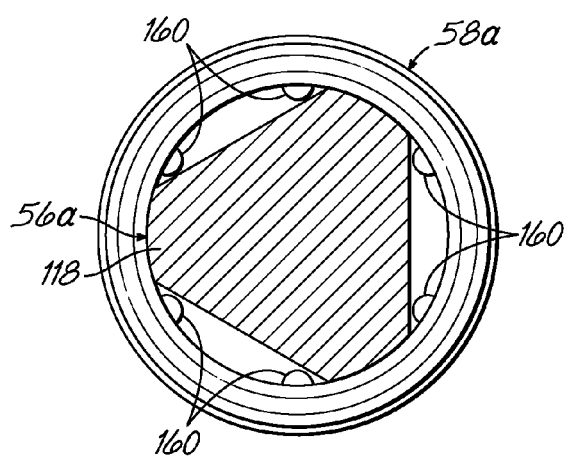
FIG. 8C is a cross-sectional view of a spigot of the spindle engaging the cap of a tube, taken along the line 8C-8C of FIG. 8A.
Figure 8:
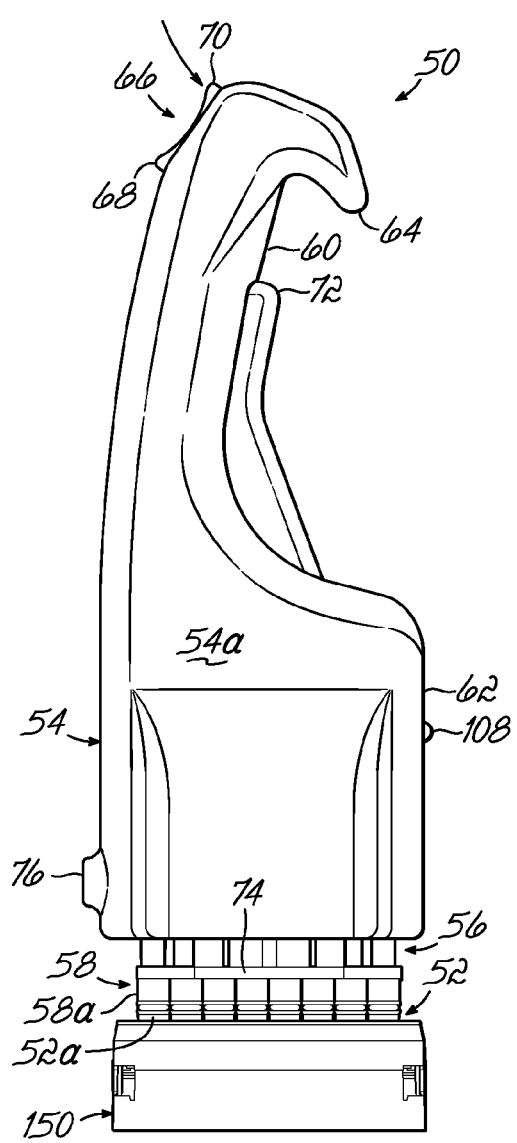

In FIG. 8, the spigots 118 engage the caps 58 and the investigator may engage the first trigger 66 in the second actuating position 70, which applies an electrical signal to the controller 104 (FIG. 2B) and/or the motor 96 for operation of the device 50 in the decapping mode.

Figure 8A:
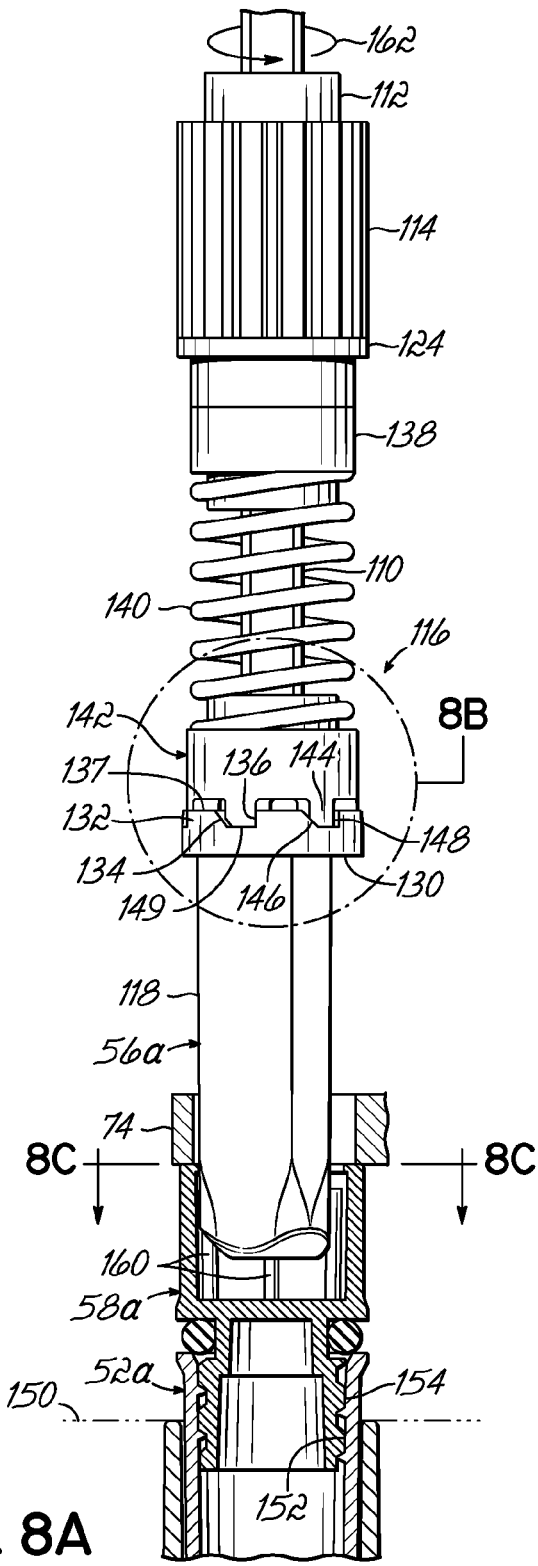
Figure 8B:
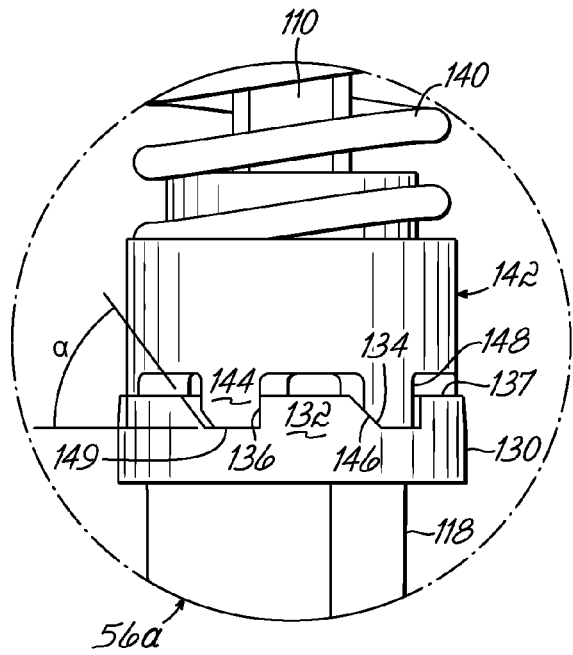
FIG. 8B is a cross-sectional view illustrating the clutch mechanism while decapping the tube.

FIGS. 8A and 8B illustrate rotation of the spindle 56a in a counterclockwise direction, as indicated by arrow 162 (FIG. 8A), which is associated with a decapping operation of the handheld device 50. With the counterclockwise rotation of the spindle 56a and corresponding shank 110, the teeth 144 of the slip gear 142 engage and apply a force to the generally vertical side 136 of the notched ring 130 of the spigot 118. Because the generally vertical side 136 is keyed to engage the generally vertical side 148 of the slip gear 142, the generally vertical sides 136, 148 provide a mechanism to fix the relative positions of the notched ring 130 and slip gear 142 so that the notched ring 130 and the slip gear 142 rotate together and the rotational force is therefore transferred to the spigot 118. The rotation of the spigot 118 is transferred through the engagement of the spigots 118 with the caps 58, which results in a decapping movement of the caps 58.

FIG. 8C illustrates the engagement between the spigot 118 and the cap 58 according to one embodiment. The spigot 118 may be constructed to include a particular key-shape, which engages and forms a frictional fit with the ribs 160 of the cap 58 so that the caps 58 are retained on the spigots 118 when the caps 58 have been decapped from the tubes 32. The key-shape of the spigot 118 may include a shape that provides some allowance in matching the ribs 160 with the caps 58, i.e., the shapes are not necessarily matching structures.

Figure 9:
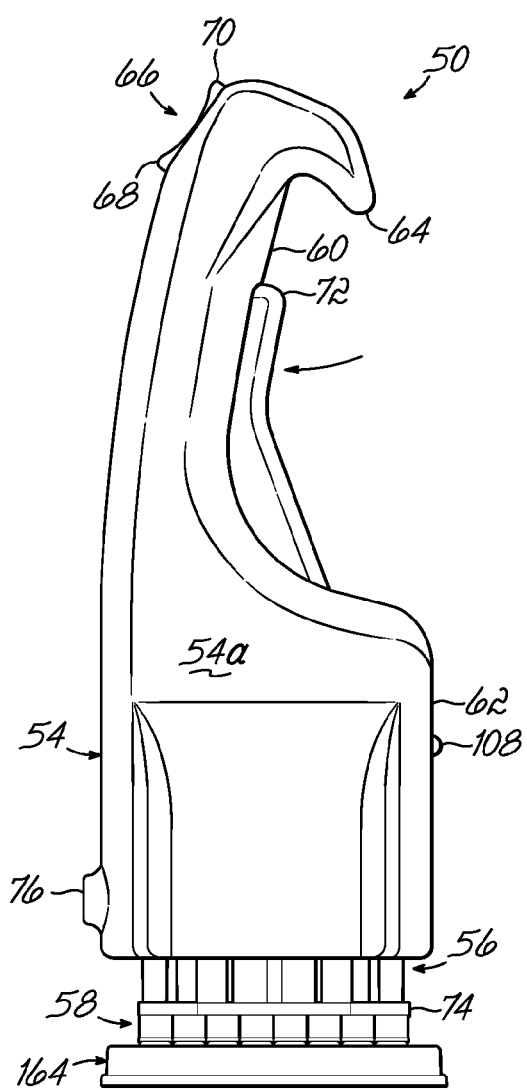
FIG. 9 is a side elevational view of one manner of releasing the caps from the handheld device.
Figure 9A:
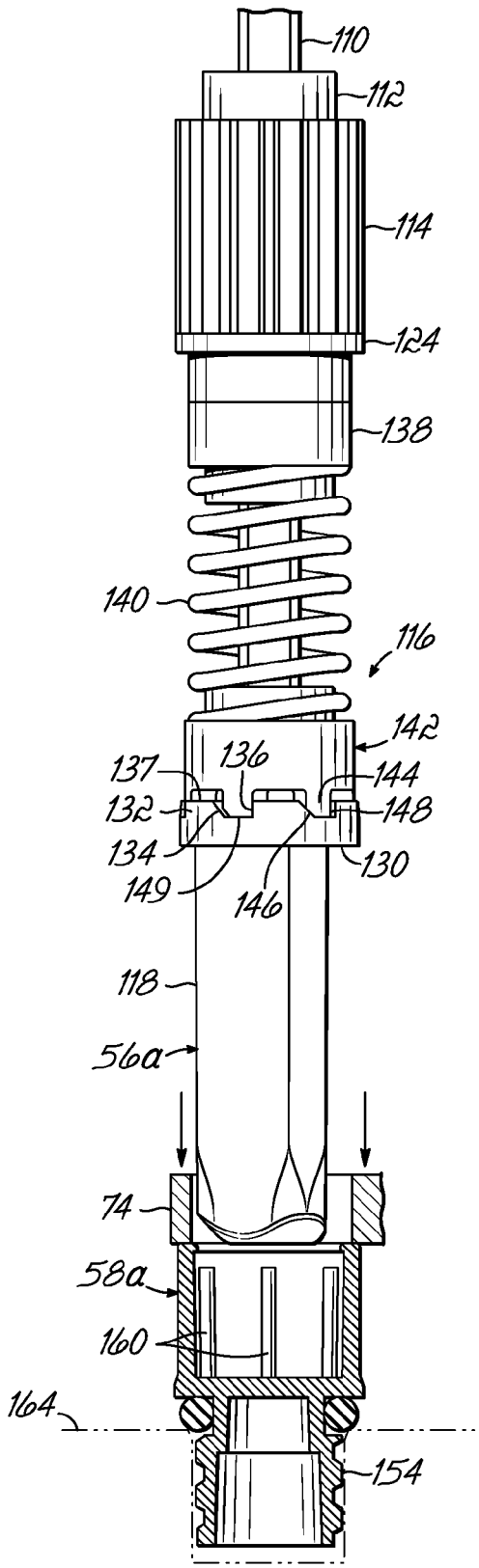
FIG. 9A is an enlarged side elevational view of releasing a cap from the spindle.

FIGS. 9 and 9A illustrate one manner of releasing the caps 58 from the spigots 118 of the handheld device 50. As described previously, as the second trigger 72 is squeezed by the user, the slider plate 80 and extension plate 90 cooperate to move the ejection plate 74 downwardly to apply a force to a top portion of the caps 58. Once the downward force exceeds the frictional force between the cap 58 and the spigot 118, the cap 58 is ejected, or released, from the spigot 118. As shown in FIG. 9, the caps 58 may be released into a storage tray 164 for later re-capping the tubes $52_a$-$52_h$. Alternatively, the caps $58_a$-$58_h$ may be deposited into a container or a waste receptacle according to lab safety protocols and standard operating procedures.

Figure 10B:
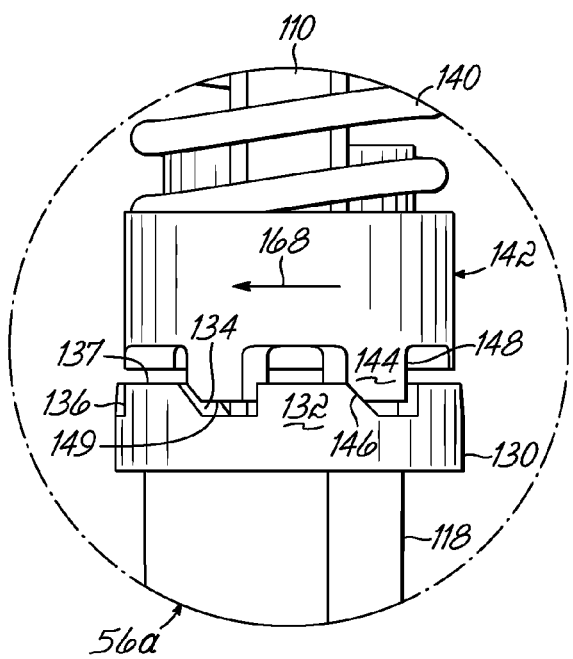
FIGS. 10B and 11B are cross-sectional views illustrating successive steps of a clutch mechanism of the spindle while engaging and tightening the cap onto the tube.
Figure 11B:
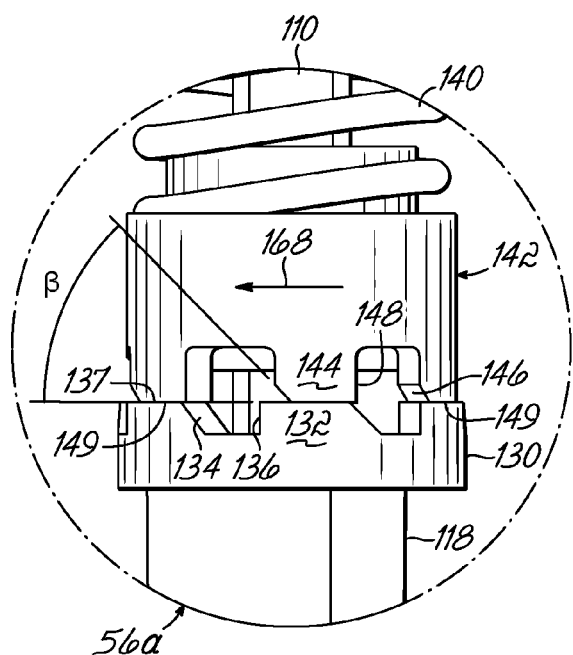
Figure 10:
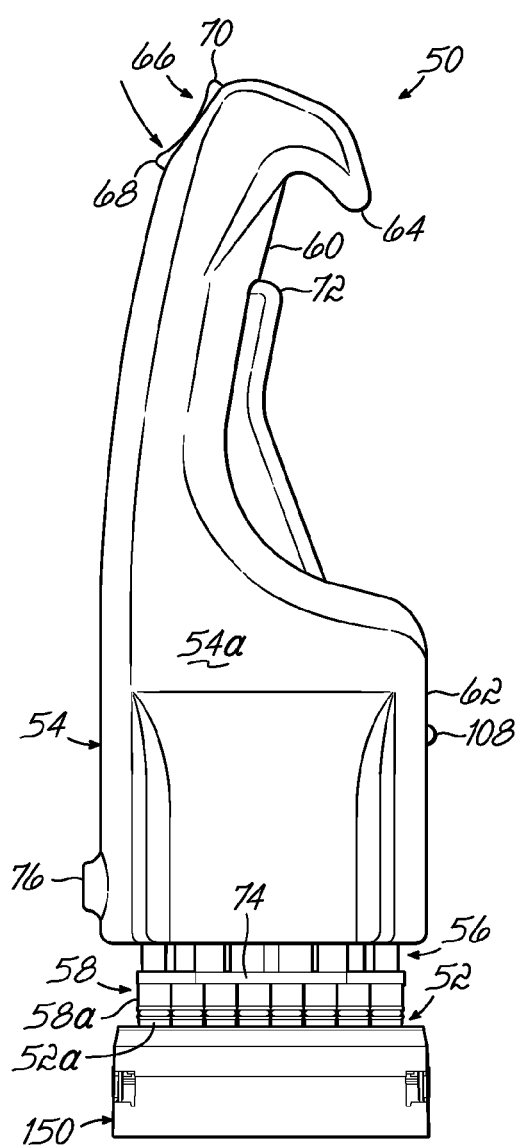
FIGS. 10 and 11 are side elevational views illustrating successive steps of the handheld device engaging and tightening the caps onto each tube of the one-dimensional array.
Figure 10A:
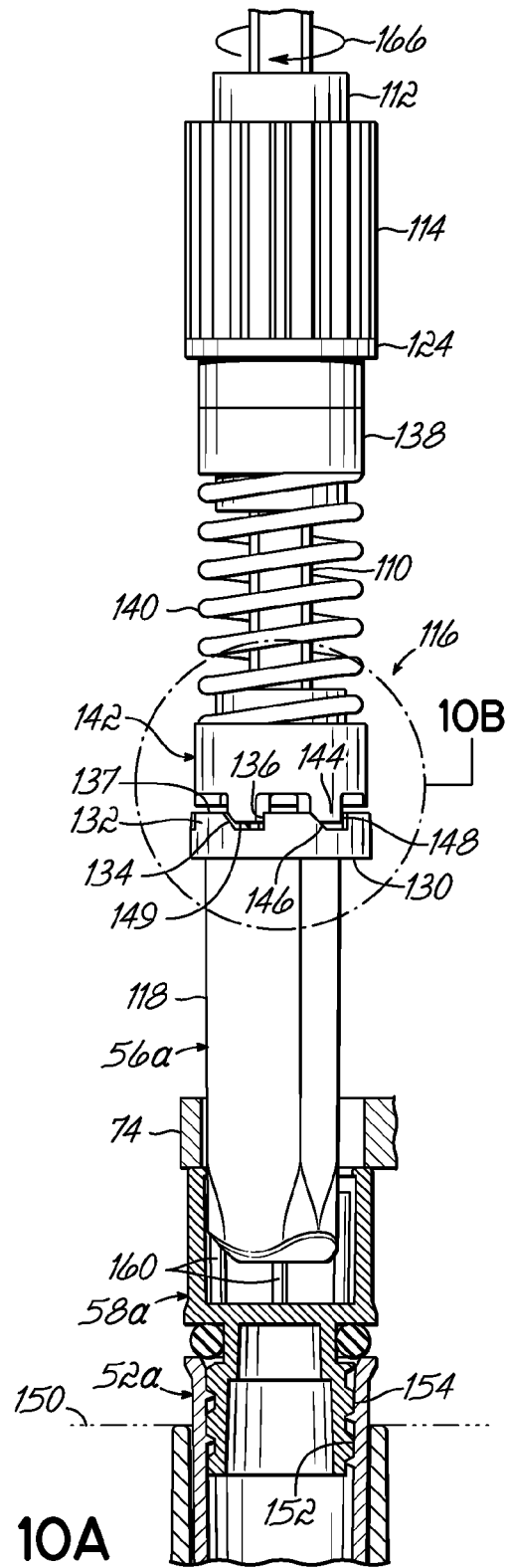
FIGS. 10A and 11A are enlarged side elevational views illustrating successive steps of one spindle engaging and tightening the cap onto a tube.
Figure 11:
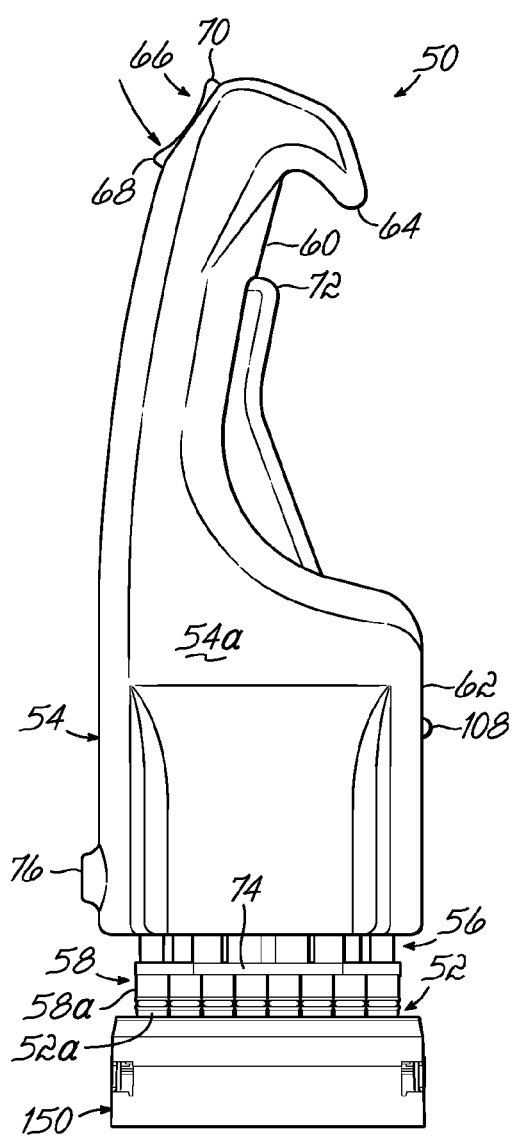

Turning now to FIGS. 10-11B, where successive steps of one exemplary manner of using the handheld device 50 to cap the array of tubes 52 are shown. In FIGS. 10 and 10A, the spigots 118 have engaged an array of caps 58 and the handheld device 50 has transferred the caps $58_a$-$58_h$ to the one-dimensional array of tubes 52. The investigator may then activate the first trigger 66 to the first actuating position 68, which applies an electrical signal to the controller 104 and/or motor 96 for operation of the device 50 in the capping mode. FIG. 10A illustrates the spigot 118 engaging the cap 58 and the spigot 118 rotating in a clockwise direction, indicated by arrow 166. Though not specifically shown, the handheld device 50 may then be separated from the one-dimensional array of capped tubes 52, which may be accomplished manually or with the ejection plate 74.

Figure 11A:
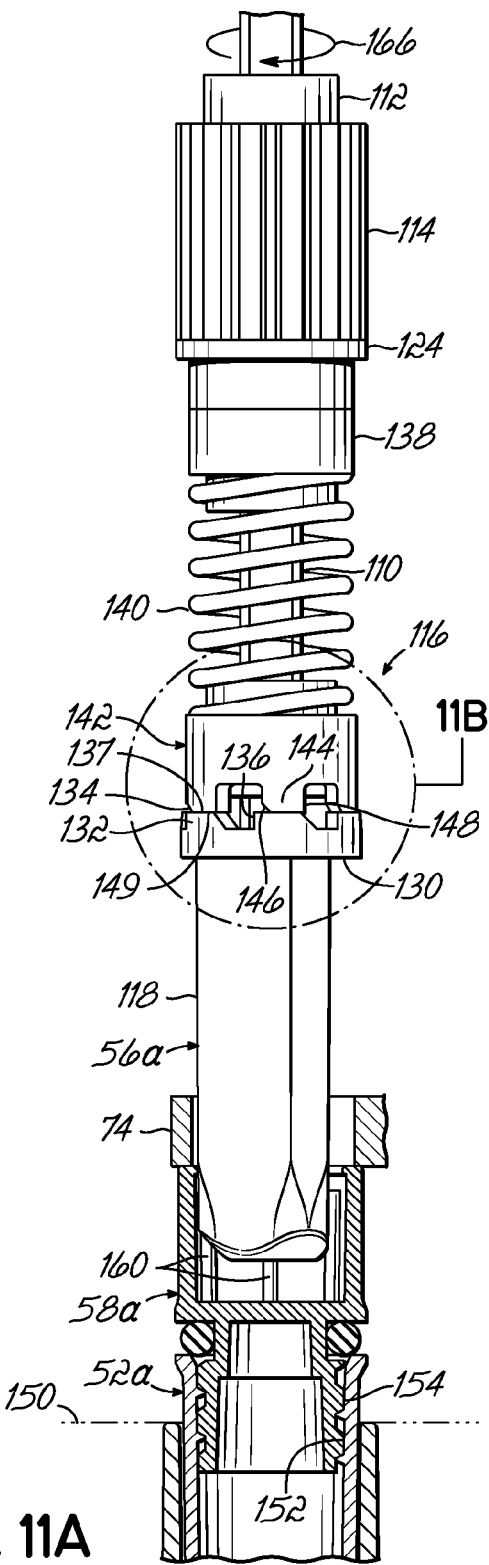

FIG. 10B illustrates the clockwise rotation of the clutch mechanism 116, indicated by arrow 168, which is associated with the capping mode with greater detail. With the clockwise rotation of the shank 110, the sloped side 146 of the slip gear 142 engages the sloped side 134 of the notched ring 130 of the spigot 118. Generally, the engaging of the sloped sides 146, 134 will transfer the clockwise rotation of the shank 110 to the spigot 118, and ultimately the cap 58 for capping the tube 52. However, once the cap 58 has fully rotated onto the thread 152 of the tube 52 and as the shank 110 continues to rotate clockwise, the amount of torque applied to the notched ring 130 of the spigot 118 meets and exceeds the spring constant of the spring 140. As a result, the sloped side 146 of the slip gear 142 moves or travels along the sloped side 134 of the notched ring 130 of the spigot 118, out of the notch 132 (see FIGS. 11A and 11B), and will then fall into an adjacent notch 132. In this way, excessive clockwise rotation of the slip gear 142 and shank 110 does not result in over-rotation of the spigot 118 and cap 58, which may lead to stripping of the thread pattern 154 of the cap 58 and/or damage to the tube 52.

As will be readily appreciated, the handheld capper/decapper device 50 provides an effective manner of capping and decapping a subset of tubes 52, particularly a one-dimensional array of tubes $52_a$-$52_h$. The handheld device 50 is easily moved and manipulated by a grasped hand of a user to transfer the caps 58 to and/or from the tubes 52. Further, it will be appreciated that the handheld device 50 facilitates the capping of the one-dimensional array of tubes $52_a$-$52_h$ without causing damage to the tubes 52 or the caps 58.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A handheld capper/decapper device for capping and decapping a plurality of threaded caps associated with a plurality of threaded receptacles, comprising:
   a handheld housing configured to be grasped and manipulated in a plurality of orientations by a user's hand;
   a one-dimensional array of rotatable spindles supported by the housing, each spindle of the one-dimensional array being configured to engage a respective one of the plurality of caps; and
   a drive mechanism operable to simultaneously rotate each spindle of the one-dimensional array in a first direction to rotate the plurality of caps relative to the plurality of receptacles to cap the plurality of caps into threaded engagement with the plurality of receptacles and in a second opposite direction to rotate the plurality of caps relative to the plurality of receptacles to decap the plurality of caps from threaded engagement with the plurality of receptacles.

2. The handheld capper/decapper device of claim 1 further comprising:
   an ejection plate configured to separate the plurality of caps from the one-dimensional array of spindles.

3. The handheld capper/decapper device of claim 2, wherein the ejection plate further comprises:
   a one-dimensional array of openings aligned with the one-dimensional array of spindles such that each spindle extends through one of the one-dimensional array of openings, wherein a diameter of each opening is sized to be greater than an outer diameter of each spindle but less than an outer diameter of each cap.

4. The handheld capper/decapper device of claim 2, further comprising a trigger configured to cooperate with the ejection plate to move the ejection plate relative to the one-dimensional array of spindles so as to separate the plurality of caps from the one-dimensional array of spindles.

5. The handheld capper/decapper device of claim 1, wherein each spindle includes a clutch mechanism, the clutch mechanism comprising:
   a compression device for defining a predetermined amount of torque to each of the plurality of caps during a capping operation; and
   a slip gear operable to prevent rotation of the one-dimensional array of spindles in a first direction so as to exceed the predetermined amount of torque, wherein the slip gear includes a mechanism configured to overcome the predetermined amount of torque when the one-dimensional array of spindles rotates in a second direction that opposes the first direction.

6. The handheld capper/decapper device of claim 5, wherein the slip gear interfaces with a notched ring of each spindle, wherein the notched ring of each spindle includes a plurality of notches with each notch includes a sloped side and a generally vertical side.

7. The handheld capper/decapper device of claim 6, wherein the slip gear engages the generally vertical side of the notched ring when decapping the one-dimensional array of receptacles and the sloped side of the notched ring when capping the one-dimensional array of receptacles.

8. The handheld capper/decapper device of claim 1, wherein the drive mechanism comprises:
   a motor;
   a drive shaft operatively coupled to the motor and one spindle of the one-dimensional array of spindles; and
   a belt transferring a rotation of the one spindle to the other spindles of the one-dimensional array of spindles.

9. The handheld capper/decapper device of claim 8, wherein each spindle includes a gear portion and the belt includes a plurality of teeth that engage the gear portion positioned on each spindle of the one-dimensional array.

10. The handheld capper/decapper device of claim 8, further comprising:
    a device that contacts the belt so as to retain the belt against each spindle of the one-dimensional array of spindles.

11. The handheld capper/decapper device of claim 1, further comprising:
    a power supply to operate the drive mechanism.

12. The handheld capper/decapper device of claim 11, wherein the power supply is one of a rechargeable power supply, an alkaline battery, or an external electrical supply.

13. A capper/decapper device having at least one spindle that includes a spigot for engaging a cap, comprising:
    a notched ring coupled to the spigot, the notched ring having a plurality of notches, wherein each notch includes a sloped side and a generally vertical side;
    a compression device; and
    a slip gear operatively coupled to the compression device and cooperating with the notched ring, the slip gear having a plurality of teeth, wherein each of the plurality of teeth includes a sloped side and a generally vertical side,
    wherein during a capping operation of the device, the notched ring and the slip gear rotate together in fixed relationship relative to each other until a torsional force applied by the slip gear to the notched ring exceeds a predetermined torque whereat the slip gear rotates relative to the notched ring.

* * * * *

UNITED STATES PATENT AND TRADEMARK OFFICE
CERTIFICATE OF CORRECTION

PATENT NO. : 8,196,375 B2
APPLICATION NO. : 12/788708
DATED : June 12, 2012
INVENTOR(S) : Kohanski et al.

It is certified that error appears in the above-identified patent and that said Letters Patent is hereby corrected as shown below:

In column 6, line 25, change "to further prevent the toothed belt 122 form disengaging" to --to further prevent the toothed belt 122 from disengaging--.

In column 6, line 40, change "or within a tray 150 containing of 96 tubes" to --or within a tray 150 containing 96 tubes--.

In column 6, line 64, change "Selection of angle "a"" to --Selection of angle "α"--, as appears in the Specification at Page 13, Paragraph [0047].

In column 10, claim 6, line 7, change "with each notch includes a sloped side" to --with each notch including a sloped side--.

Signed and Sealed this
Seventh Day of August, 2012

David J. Kappos
*Director of the United States Patent and Trademark Office*